United States Patent [19]

Ilvespaa

[11] B 3,996,238

[45] Dec. 7, 1976

[54] 4- OR 5-NITROIMIDAZOLES AND PROCESSES FOR THEIR MANUFACTURE

[75] Inventor: Atso Ilvespaa, Neuallschwil, Switzerland

[73] Assignee: Ciba-Geigy Corporation, Ardsley, N.Y.

[22] Filed: Nov. 11, 1974

[21] Appl. No.: 522,567

[44] Published under the second Trial Voluntary Protest Program on February 17, 1976 as document No. B 522,567.

Related U.S. Application Data

[62] Division of Ser. No. 328,816, Jan. 31, 1973, Pat. No. 3,914,248.

[30] Foreign Application Priority Data

Feb. 8, 1972  Switzerland ............... 1810/72

[52] U.S. Cl. .............. 260/309.2; 260/243 B; 260/243 R; 260/247; 260/248 AS; 260/248 NS; 260/250 A; 260/250 R; 260/256.4 R; 260/293.7; 260/296 R; 260/302 D; 260/302 F; 260/302 H; 260/306.7 R; 260/307 R; 260/309.6; 424/246; 424/251; 424/263; 424/264; 424/272; 424/273; 424/274; 424/275; 424/285

[51] Int. Cl.² ................... C07D 49/34
[58] Field of Search ................ 260/309.2

[56] References Cited
UNITED STATES PATENTS 3,832,352  8/1974  Ilvespaa ............ 260/309.7

FOREIGN PATENTS OR APPLICATIONS 1,920,635  10/1970  Germany ............ 260/309.2
1,078,251  8/1967   United Kingdom .... 260/309.2

Primary Examiner—Ethel G. Love
Attorney, Agent, or Firm—Joseph G. Kolodny; John J. Maitner; Theodore O. Groeger

[57] ABSTRACT

4- or 5-nitro-imidazoles of the formula I

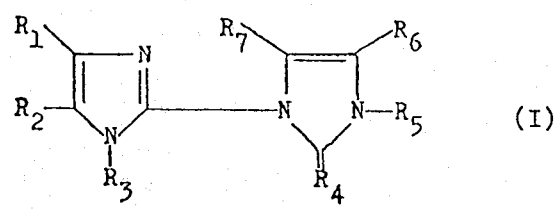

wherein one of the radicals $R_1$ and $R_2$ is hydrogen or lower alkyl and $R_2$ is the nitro group or $R_1$ is the nitro group and $R_2$ is hydrogen or lower alkyl, $R_3$ is lower alkyl, hydroxy-lower alkyl, lower alkoxy-lower alkyl, lower alkylsulphonyl-lower alkyl, dilower alkylamino-lower alkyl, lower alkylene-amino-lower alkyl, lower oxaalkyleneamino-lower alkyl, lower thiaalkyleneamino-lower alkyl or lower azaalkyleneamino lower alkyl, $R_4$ is oxo or thioxo and $R_5$ is a phenyl radical which optionally has one, two or more substituents, an optionally substituted furyl, thienyl, pyrrolyl, indolyl, oxazolyl, thiazolyl, thiadiazolyl, 4,5-dihydro-thiazolyl-(2), tetrahydro-thiazolyl-(2), pyrazolyl, indazolyl, imidazolyl-(5), imidazolyl-(4), pyridyl, pyrazinyl, pyrimidinyl, pyridazinyl, 1,3,5- or 1,2,4-triazinyl, pyrrolidinyl, pyrazolinyl, indolinyl, pyrazolidinyl, imidazolinyl, imidazolidinyl, piperidyl, morpholinyl, thiazinyl, thiomorpholinyl or piperazinyl radical, an optionally C-lower alkylated pyrrolidino, piperidino, morpholino, thiomorpholino, piperazino, N'-lower alkyl-piperazino, N'-β-hydroxyethyl-piperazino or pyridinium radical and $R_6$ and $R_7$ independently of one another denote hydrogen or lower alkyl or conjointly form the missing part of a fused benzene nucleus which is optionally substituted by lower alkyl, lower alkoxy, halogen, trifluoromethyl and/or nitro, as well as their S-oxides, sulphones N-oxides and/or acid addition salts thereof, which are useful as agents against schistosomes, filaria, trichomonades, bacteriae, and/or amoebae.

4 Claims, No Drawings

4-OR 5-NITROIMIDAZOLES AND PROCESSES FOR THEIR MANUFACTURE

This is a division of application Ser. No. 328,816, filed Jan. 31, 1973, now U.S. Pat. No. 3,914,248.

The subject of the invention are new 4- or 5-nitroimidazoles of the formula I

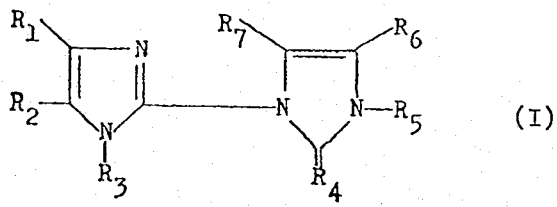

wherein one of the radicals $R_1$ and $R_2$ is hydrogen or lower alkyl and the other is the nitro group, $R_3$ is hydrogen or optionally substituted lower alkyl, $R_4$ is oxo or thioxo, $R_5$ is hydrogen, optionally substituted lower alkyl or phenyl, acyl or a heterocyclic radical and $R_6$ and $R_7$ independently of one another denote hydrogen or lower alkyl or conjointly denote the missing part of an optionally substituted fused benzene nucleus, and processes for their manufacture.

In the preceding and following text, a lower radical such as, for example, a lower alkyl radical, is to be understood as a radical, for example an alkyl radical, which contains not more than eight and especially not more than four carbon atoms.

Lower alkyl is hence straight-chain or branched octyl, heptyl, hexyl, pentyl or in particular butyl or propyl, bonded in any desired position, or especially ethyl or methyl. Substituted lower alkyl is in particular lower alkyl which carries one or more substituents which can be identical or different. As such substitutents there should in particular be mentioned: aryl, above all optionally substituted phenyl, the hydroxyl and mercapto group, halogen, above all fluorine, chlorine or bromine, lower alkoxy, above all butoxy, propoxy, isopropoxy or especially ethoxy or methoxy, alkylmercapto, such as, for example, the mercapto group substituted by lower alkyl, above all butylmercapto, propylmercapto, isopropylmercapto or especially ethylmercapto or methylmercapto, the free amino group, secondary amino groups, above all optionally substituted anilino groups or lower alkylamino groups, such as butylamino, propylamino, isopropylamino or especially ethylamino or methylamino, the free amino group, or tertiary amino groups, such as optionally substituted N-lower alkylanilino groups, for example the N-butyl-, N-propyl-, N-isopropyl- or especially N-ethyl- or N-methylanilino group or above all di-lower alkylamino groups, for example dibutylamino, diisobutylamino, dipropylamino, diisopropylamino, ethylmethylamino or especially diethylamino or dimethylamino, and also especially alkyleneamino and oxaalkyleneamino, azaalkyleneamino or thiaalkyleneamino groups, such as the optionally C-methylated pyrrolidino, piperidino, morpholino, thiomorpholino, 2,6-dimethylthiomorpholino, piperazino, N'-methylpiperazino or N'-β-(hydroxyethyl)-piperazino group, or sulphonyl groups, such as arylsulphonyl groups, for example optionally substituted benzenesulphonyl groups, or alkanesulphonyl groups, above all lower alkanesulphonyl groups, for example the methanesulphonyl or ethanesulphonyl group.

Acyl is, in particular, the radical of a carboxylic acid derived from an aromatic or aliphatic hydrocarbon radical, above all an aroyl group, such as, for example, an optionally substituted benzoyl group, or an alkanoyl group, especially a lower alkanoyl group, such as, for example, valeroyl, isovaleroyl, pivaloyl, butyryl, isobutyryl, propionyl, formyl and especially acetyl, or the radical of an organic sulphonic acid, above all of an aromatic sulphonic acid such as, for example, of benzenesulphonic acid, toluenesulphonic acid or bromobenzenesulphonic acid, or of an aliphatic sulphonic acid, for example of methanesulphonic acid or ethanesulphonic acid.

By optionally substituted phenyl or benzoyl or an optionally substituted fused benzene ring there are to be understood both these groups themselves and also phenyl groups, benzoyl groups and fused benzene rings substituted by one, two or more than two identical or different substituents, such as lower alkyl, lower alkoxy, halogen, above all chlorine or bromine, nitro and-/or trifluoromethyl.

Possible halogen atoms are especially fluorine or bromine atoms and above all chlorine atoms.

A heterocyclic radical is especially a heteroaromatic or heteroaliphatic radical. Heterocyclic radicals are bonded via an atom which is a member of a heterocyclic ring.

A heteroaryl radical $R_5$ is, for example, a mononuclear or polynuclear radical of aromatic character which contains, as a constituent, at least one heterocyclic ring of aromatic character possessing a heteroatom. Suitable hetero-atoms are, for example, oxygen, sulphur and/or nitrogen atoms.

Suitable radicals of this nature are, for example, radicals possessing at least one five-membered ring containing at least one hetero-atom, especially one of those mentioned above, such as furyl, benzo[b]furyl, thienyl, benzo[b]thienyl, pyrrolyl, indolyl, oxazolyl, thiazolyl, isooxazolyl, isothiazolyl, pyrazolyl, 3H-pyrazolyl, indazolyl, and imidazolyl radicals, above all 2-imidazolyl radicals which can also be substituted in the 1-position, especially by acyl, lower alkyl or substituted lower alkyl, in one of positions 4 or 5 by lower alkyl and in the other of the positions mentioned by lower alkyl or by the nitro group, and also furazanyl and triazolyl radicals, such as, for example, 1H- or 2H-1,2,4-triazolyl radicals, thiadiazolyl radicals and tetrazolyl radicals, as well as radicals possessing at least one six-membered ring which contains at least one hetero-atom, especially one of those mentioned above, such as pyridyl, quinolyl, isoquinolyl, acridinyl, pyrazinyl, pyrimidinyl, pyridazinyl, quinoxalinyl, phenazinyl, 1,3,5- and 1,2,4-triazinyl radicals.

The heterocyclic radicals of aromatic character can have one, two or more substituents but are preferably unsubstituted.

Possible substituents on carbon atoms of the heteroaryl radicals mentioned are especially lower alkoxy groups, such as methoxy, ethoxy, propoxy and butoxy groups, trifluoromethyl groups, optionally substituted amino groups or nitro groups, and especially hydroxyl groups, halogen atoms, such as fluorine, chlorine and bromine atoms, and above all lower alkyl radicals, such as methyl, ethyl, propyl and isopropyl radicals, straight and branched butyl, pentyl and hexyl radicals bonded in any desired position, as well as phenyl radicals optionally substituted by lower alkyl, lower alkoxy, halogen or trifluoromethyl groups, and mercapto groups.

Optionally substituted amino groups are, for example, mono- and di-lower alkylamino groups as well as acylamino groups and N-acyl-N-lower and alkylamino groups, such as methyl-, ethyl-, dimethyl-, diethyl-, lower alkanoyl-, for example acetyl-, N-lower alkanoyl-N-lower alkyl-, for example N-acetyl-N-methyl-, benzoyl- and N-benzoyl-N-methyl-amino groups.

In heterocyclic radicals which carry a hydrogen atom on a ring nitrogen atom, the hydrogen atom can also be replaced by lower alkyl radicals or acyl radicals, especially benzoyl radicals which are optionally substituted, for example substituted as indicated above for the aryl radicals, and above all lower alkanoyl radicals, for example propionyl, butyryl and especially acetyl radicals.

In heterocyclic radicals, oxidisable hetero-atoms can also be present in the form of their oxides. Thus, in particular, sulphur atoms can be S-oxidised or S-dioxidised and above all nitrogen atoms can be N-oxidised.

The free valency of the heterocyclic radicals of aromatic character in particular starts from a C atom belonging to the aromatic system.

A heteroaliphatic radical $R_5$ is, for example, a monocyclic or polycyclic radical of aliphatic character which contains, as a constituent, at least one heterocyclic ring of aliphatic character possessing at least one heteroatom, such as one of those mentioned above.

Suitable radicals of this nature are, for example, radicals possessing at least one five-membered ring which contains at least one hetero-atom, especially one of those mentioned above, such as tetrahydrofuryl, tetrahydrothienyl, pyrrolidinyl, indolinyl, pyrazolinyl, pyrazolidinyl, 4,5-alkylenethiazolyl-(2), 4,5-dihydrothiazolyl, tetrahydrothiazolyl, imidazolinyl and imidazolidinyl radicals, as well as radicals possessing at least one six-membered ring which contains at least one hetero-atom, especially one of those mentioned above, such as pyranyl, for example 2H- and 4H-pyranyl, tetrahydropyranyl, thiopyranyl, for example 2H- and 4H-thiopyranyl, tetrahydrothiopyranyl, tetrahydropyridyl, for example 1,2,3,4-tetrahydropyridyl, piperidyl, 1,2,3,4-tetrahydroquinolyl, oxazinyl, such as 2H-1,2-, 4H-1,2-, 6H-1,2-, 2H-1,3-, 4H-1,3- and 4H-1,4-oxazinyl, morpholinyl, thiazinyl, for example 2H-1,3-thiazinyl, thiomorpholinyl and piperazinyl radicals.

The heteroaliphatic radicals can have one, two or more substituents but are preferably unsubstituted.

Possible substituents on carbon atoms of the heteroaliphatic radicals mentioned are in particular alkoxy radicals, halogen atoms, hydroxyl groups and optionally substituted amino groups, such as those mentioned above, and above all lower alkyl radicals, such as those mentioned above.

Ring nitrogen atoms carrying a hydrogen atom can be substituted, especially as indicated above, and oxidisable hetero-atoms can be present in the form of their oxides, especially as indicated above.

The free valency of the heteroaliphatic radicals in particular starts from a C atom belonging to the heterocyclic structure.

The new imidazoles possess valuable pharmacological properties. Thus they show, in particular, actions against bacteria, especially Gram-negative germs, protozoa and worms, such as trichomonades, schistosomes, coccidia, filaria and above all amoebae, as can be shown in animal experiments, for example on hamsters. The new imidazoles are therefore useful as agents against schistosomes, filaria, trichomonades, bacteria and especially against amoebae. Furthermore, the new imidazoles can serve as starting products or intermediate products for the manufacture of other compounds, especially therapeutically active compounds.

A preferred group is the group Ia of those compounds of the formula I wherein one of the radicals $R_1$ and $R_2$ is hydrogen or lower alkyl and the other is the nitro group, $R_3$ is hydrogen, optionally substituted lower alkyl or acyl, $R_4$ is oxo or thioxo, $R_5$ is hydrogen, optionally substituted lower alkyl or phenyl, acyl or a heteroaryl and $R_6$ and $R_7$ independently of one another denote hydrogen or lower alkyl or conjointly denote the missing part of an optionally substituted fused benzene nucleus.

A group to be singled out is the group Ib of those compounds of the formula I wherein $R_1$ is hydrogen or lower alkyl and $R_2$ is the nitro group or $R_1$ is the nitro group and $R_2$ is hydrogen or lower alkyl, $R_3$ is hydrogen, lower alkyl, hydroxy-lower alkyl, amino-lower alkyl, mono- or di-lower alkyl-amino-lower alkyl, alkyleneamino-lower alkyl, optionally C-methylated morpholino-, thiomorpholino- or N'-methylpiperazino-lower alkyl, lower alkoxy-lower alkyl, halogeno-lower alkyl or lower alkylmercapto-lower alkyl, $R_4$ is oxo or thioxo, $R_5$ has one of the meanings indicated for $R_3$, is lower alkanoyl or benzoyl optionally substituted by lower alkyl, lower alkoxy, halogen, trifluoromethyl and/or nitro or denotes a phenyl or 2-imidazolyl radical which is optionally substituted by lower alkyl, lower alkoxy, halogen, trifluoromethyl and/or nitro and $R_6$ and $R_7$ independently of one another denote hydrogen or lower alkyl or conjointly form the missing part of a fused benzene nucleus which is optionally substituted by lower alkyl, lower alkoxy, halogen, trifluoromethyl and/or nitro.

A further group to be singled out is the group Ic of those compounds of the formula I wherein $R_1$ is hydrogen or lower alkyl and $R_2$ is the nitro group or $R_1$ is the nitro group and $R_2$ is hydrogen or lower alkyl, $R_3$ is lower alkyl, hydroxy-lower alkyl, lower alkoxy-lower alkyl, lower alkylsulphonyl-lower alkyl, di-lower alkylamino-lower alkyl, lower alkylene-amino-lower alkyl, lower oxaalkyleneamino-lower alkyl, lower thiaalkyleneamino-lower alkyl or lower azaalkyleneamino-lower alkyl, $R_4$ is oxo or thioxo and $R_5$ is a phenyl radical which optionally has one, two or more substituents, an optionally substituted furyl, thienyl, pyrrolyl, indolyl, oxazolyl, thiazolyl, thiadiazolyl, 4,5-dihydro-thiazolyl-(2), tetrahydro-thiazolyl-(2), pyrazolyl, indazolyl, imidazolyl-(5), imidazolyl-(4), pyridyl, pyrazinyl, pyrimidinyl, pyridazinyl, 1,3,5- or 1,2,4-triazinyl, pyrrolidinyl, pyrazolinyl, indolinyl, pyrazolidinyl, imidazolinyl, imidazolidinyl, piperidyl, morpholinyl, thiazinyl, thiomorpholinyl or piperazinyl radical, an optionally C-lower alkylated pyrrolidino, piperidino, morpholino, thiomorpholino, piperazino, N'-lower alkyl-piperazino, N'-β-hydroxyethyl-piperazino or pyridinium radical and $R_6$ and $R_7$ independently of one another denote hydrogen or lower alkyl or conjointly form the missing part of a fused benzene nucleus which is optionally substituted by lower alkyl, lower alkoxy, halogen, trifluoromethyl and/or nitro, as well as their S-oxides, sulphones and N-oxides.

A group which is especially suitable is the group Id of those compounds of the formula I wherein $R_1$ is hydrogen or lower alkyl and $R_2$ is the nitro group or $R_1$ is the nitro group and $R_2$ is hydrogen or lower alkyl, $R_3$ hydrogen, lower alkyl, hydroxy-lower alkyl, above all 2-hydroxypropyl, 1- or 2-hydroxyethyl or hydroxymethyl, amino-, mono-, or di-lower alkylamino-, pyrrolidino-, piperidino-, morpholino-, thiomorpholino- or N'-methylpiperazino-lower alkyl, above all -methyl or -ethyl, chloro- or bromo-lower alkyl, above all -ethyl, or lower alkoxy-lower alkyl, above all methoxy- or ethoxy-lower alkyl, $R_4$ is oxo or thioxo, $R_5$ has one of the meanings indicated for $R_3$ or is a radical of the formula

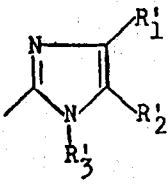

wherein $R_1'$ is hydrogen or lower alkyl, $R_3'$ has one of the meanings indicated for $R_3$ or is lower alkanoyl or aroyl, such as benzoyl optionally substituted by lower alkyl, lower alkoxy, halogen, trifluoromethyl and/or nitro, $R_2'$ is hydrogen or the nitro group and $R_6$ and $R_7$ independently of one another denote hydrogen or lower alkyl or conjointly form the missing part of a fused benzene nucleus which is optionally substituted by lower alkyl, lower alkoxy, halogen, trifluoromethyl and/or nitro.

Amongst the abovementioned compounds of the group I$d$ there should in turn be singled out the group I$e$, wherein $R_5$ is a radical of the formula

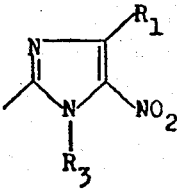

the symbols $R_1$, $R_2$, $R_3$ and $R_4$ have the meanings indicated for the group Id and $R_6$ and $R_7$ denote hydrogen or conjointly denote the missing part of a fused benzene nucleus.

A further group which is particularly suitable is the group I$f$ of those compounds of the formula I wherein $R_1$ is hydrogen or lower alkyl and $R_2$ is the nitro group or $R_1$ is the nitro group and $R_2$ is hydrogen or lower alkyl, $R_3$ is hydroxy-lower alkyl or lower alkyl, $R_4$ is oxo or thioxo and $R_5$ is hydrogen, lower alkyl, hydroxy-lower alkyl, lower alkoxy-lower alkyl, propionyl, butyryl, acetyl, formyl, phenyl, o-, m- or p-fluorophenyl, 4-thiazolyl, 2-thiazolyl, 4,5-dimethyl-thiazolyl-(2), 5,6-dihydro-4H-cyclopenta-thiazolyl-(2), 5-amino-1,3,4-thiadiazolyl-(2), 4,5-dihydro-thiazolyl-(2), tetrahydro-thiazolyl-(2), 4-acetyl-thizolyl-(2), 5-acetyl-thiazolyl-(2), 5-methylsulphonyl-thiazolyl-(2), pyridyl-(2), pyridyl-(3), pyridyl-(4), 4,6-dimethyl-pyridyl-(2), 3,5-dimethylpyridyl-(2), pyrimidinyl-(2), pyrimidinyl-(5), 2,6-dihydroxy-pyrimidinyl-(4), 2,4-dimethyl-pyrimidinyl-(5), 4,6-dimethyl-pyrimidinyl-(2), pyrrolidinyl-(2), piperidyl-(3), imidazolyl-(2), imidazolyl-(4), imidazolyl-(5), 1,3,4-thiadiazolyl-(2), 5-methyl-1,3,4-thiadiazolyl-(2), 5-ethyl-1,3,4-thiadiazolyl-(2) or an optionally C-lower alkylated pyrrolidino, piperidino, morpholino, thiomorpholino, for example 2,6-dimethyl-thiomorpholino, piperazino, N'-lower alkyl-piperazino, N'-β-hydroxyethylpiperazino or pyridinium radical and $R_6$ and $R_7$ independently of one another denote hydrogen or lower alkyl or conjointly form the missing part of a fused benzene nucleus which is optionally substituted by lower alkyl, lower alkoxy, halogen, trifluoromethyl and/or nitro, as well as their S-oxides, sulphones and N-oxides.

However, a group which is suitable above all is the group I$g$ of those compounds of the formula I wherein $R_1$ is hydrogen or lower alkyl and $R_2$ is the nitro group or $R_1$ is the nitro group and $R_2$ is hydrogen or lower alkyl, $R_4$ is oxo or thioxo, $R_3$ and $R_5$ independently of one another are hydrogen, lower alkyl, 2-hydroxyethyl or 2-hydroxypropyl, hydroxymethyl, 2-di-lower alkylaminoethyl or 2-di-lower alkylaminopropyl or di-lower alkylaminomethyl and $R_5$ can also be lower alkanoyl, and $R_6$ and $R_7$ independently of one another denote hydrogen or lower alkyl or conjointly form the missing part of a fused benzene nucleus.

Of the abovementioned compounds of the group I$g$ there should in turn be singled out the group I$h$, wherein $R_1$ is hydrogen or methyl and $R_2$ is the nitro group or $R_1$ is the nitro group and $R_2$ is hydrogen or methyl, $R_4$ is oxo or thioxo, $R_3$ and $R_5$ independently of one another denote lower alkyl, hydroxymethyl or hydroxyethyl and $R_5$ can also be lower alkanoyl and $R_6$ and $R_7$ are hydrogen.

However, a group which is suitable above all is also the group I$i$ of those compounds of the formula I wherein $R_1$ is hydrogen or methyl and $R_2$ is the nitro group or $R_1$ is the nitro group and $R_2$ is hydrogen or methyl, $R_3$ is 2-hydroxyethyl or methyl, $R_4$ is oxo or thioxo and $R_5$ is hydrogen, methyl, hydroxymethyl, propionyl, acetyl, formyl, phenyl, p-fluorophenyl, thiazolyl-(2), 4,5-dimethyl-thiazolyl-(2), 5,6-dihydro-4-H-cyclopenta-thiazole-(2), 5-acetyl-thiazolyl-(2), 5-methylsulphonyl-thiazolyl-(2), pyridyl-(2), 4,6-dimethylpyridyl-(2), pyrimidinyl-(2), pyrimidinyl-(5), 4,6-dimethyl-pyrimidinyl-(2), 2,4-dimethyl-pyrimidinyl-(5), pyrrolidinyl-(2), piperidyl-(3), imidazolyl-(2), imidazolyl-(4), imidazolyl-(5), 1,3,4-thiadiazolyl-(2), 5-ethyl-1,3,4-thiadiazolyl-(2) or a pyrrolidino, piperidino, morpholino, thiomorpholino, 2,6-dimethyl-thiomorpholino, piperazino, N'-methyl-piperazino, N'-β-hydroxyethylpiperazino or pyridinium radical and $R_6$ and $R_7$ are hydrogen, as well as their S-oxides, sulphones and N-oxides.

However, a group which deserves very particular mention is the group I$j$ of those compounds of the formula I wherein $R_1$ is hydrogen and $R_2$ is the nitro group or $R_1$ is the nitro group and $R_2$ is hydrogen, $R_3$ is hydrogen or above all lower alkyl with 1–4 carbon atoms, $R_4$ is oxo or above all thioxo, $R_5$ is lower alkyl with 1–4 carbon atoms, above all methyl, or phenyl which is optionally substituted by methyl, methoxy, chlorine, bromine or trifluoromethyl but is above all unsubstituted and $R_6$ and $R_7$ denote hydrogen, in particular 1-methyl-3-(1-methyl-5-nitro-2-imidazolyl)-benzimidazol-2-(3H)-one, 1-methyl-3-(1-methyl-5-nitro-2-imidazolyl)-benzimidazole-2-(3H)-thione, 1-methyl-3-(1-methyl-5-nitro-2-imidazolyl)-4-imidazolin-2-one and very particularly 1-phenyl-3-(1-methyl-5-nitro-2-imidazolyl)-4-imidazoline-2-thione, 1-methyl-3-(1-methyl-4-nitro-2-imidazolyl)-4-imidazoline-2-thione and 1-methyl-3-(1-methyl-5-nitro-2-imidazolyl)-4-imidazoline-2-thione.

The new 4- or 5-nitroimidazoles of the formula I are obtained according to processes which are in themselves known.

Thus, for example, the new 4- or 5-nitro-imidazoles can be manufactured by condensing a compound of the formula II

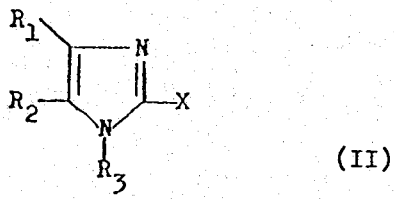

with a compound of the formula III or a tautomeric compound of the formula IIIa

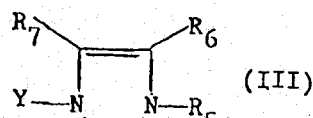

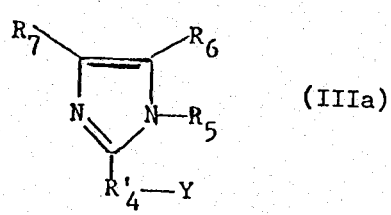

wherein $R_1$, $R_2$, $R_3$, $R_4$, $R_5$, $R_6$ and $R_7$ have the indicated meanings, $R_4'$ is an oxygen atom or above all a sulphur atom, Y is a metal atom, for example an alkali metal atom or alkaline earth metal atom or especially a hydrogen atom and X is a reactive etherified hydroxyl group, a free or etherified mercapto group, an ammonium group or especially a reactive esterified hydroxyl group or a sulphonyl group.

A reactive etherified hydroxyl group is, for example, a hydroxyl group etherified with an aromatic or aliphatic alcohol, above all with a lower aliphatic alcohol, such as an optionally substituted phenoxy group or an alkoxy group, above all a lower alkoxy group, especially methoxy or ethoxy.

An etherified mercapto group is, for example, an optionally substituted phenylmercapto or benzylmercapto group or in particular a lower alkylmercapto group, such as the ethylmercapto or methylmercapto group.

An ammonium group is, in particular, a quaternary ammonium group, above all a tri-lower alkylammonium group, for example the trimethylammonium or triethylammonium group or the cation of an aromatic nitrogen base, for example the pyridinium or quinolinium group.

A reactive esterified hydroxyl group is, in particular, a hydroxyl group esterified by a strong inorganic or organic acid, above all a hydrogen halide acid, such as hydrochloric acid, hydrobromic acid or hydriodic acid, or an organic sulphonic acid, especially an aromatic sulphonic acid, for example benzenesulphonic acid, p-bromobenzenesulphonic acid or p-toluenesulphonic acid, or an alkanesulphonic acid, above all a lower alkanesulphonic acid, for example methanesulphonic acid, ethanesulphonic acid or an olefinic sulphonic acid, for example ethenesulphonic acid.

A sulphonyl group is especially a sulphonyl group derived from an organic sulphonic acid, especially from an aromatic sulphonic acid, for example benzenesulphonic acid, p-bromobenzenesulphonic acid or p-toluenesulphonic acid, from an alkanesulphonic acid, above all a lower alkanesulphonic acid, for example methanesulphonic acid or ethanesulphonic acid, or from an olefinic sulphonic acid, for example ethenesulphonic acid.

The reaction can be carried out in the usual manner. Thus, in the reaction of a compound of the formula II with a compound of the formula III or IIIa, wherein Y is hydrogen, a basic condensation agent is preferably present, or the compound of the formula III or IIIa is reacted in the form of a salt, for example of a metal salt, such as of an alkali metal salt or alkaline earth metal salt, which is obtainable, for example, from a compound of the formula III or IIIa and a strong base, for example an amide, a hydrocarbon compound, an alcoholate, the hydroxide or especially the hydride of a metal, for example of an alkali metal, such as of lithium, potassium or above all sodium, or of an alkaline earth metal, such as of magnesium of calcium, or the metal itself, and can be used without isolation. Examples of basic condensation agents are alkali metal hydroxides or alkaline earth metal hydroxides, such as sodium hydroxide, potassium hydroxide and calcium hydroxide, or organic tertiary nitrogen bases, such as trialkylamines, for example, triethylamine or trimethylamine, or aromatic nitrogen bases, for example pyridine or quinoline. It is furthermore also possible to use an excess of the compound of the formula III or IIIa, especially if $R_5$ is not hydrogen. The reaction is advantageously carried out at elevated temperature and/or in the presence of an inert solvent, especially of an inert polar solvent, for example of acetonitrile, dimethylsulphoxide, tetramethylurea, of a higherboiling ether, for example of dioxane, diphenyl ether, diisopropyl ether or an ether of ethylene glycol, or of tetrahydrofurane, of water, of a higher alcohol, of one of the nitrogen bases mentioned or especially of dimethylformamide.

When starting from the compounds of the formula III or IIIa, wherein Y and $R_5$ denote hydrogen it is possible, on suitably choosing the reaction conditions and using double molar amounts of a compound of the formula II, to obtain both 1-mono-(4- or 5-nitro-2-imidazolyl)-4-imidazolin-2-ones or-thiones and 1,3-bis-(4- or 5-nitro-2-imidazolyl)-4-imidazolin-2-ones or -thiones of the formula I.

Furthermore, the new 4- or 5-nitro-imidazoles can be obtained, for example, if a compound of the formula IV

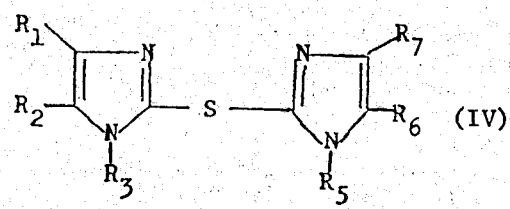

wherein $R_1$, $R_2$, $R_3$, $R_5$, $R_6$ and $R_7$ have the indicated meanings is isomerised.

The isomerisation can be carried out in the usual manner, for example thermally. Preferably, this is done at an elevated temperature, for example between 50° and 250°C, and in the presence of a catalyst, such as catalytic amounts of a halogen, especially of iodine, or of a basic condensation agent, such as, for example of an alkali metal hydroxide or alkaline earth metal hydroxide, for example of sodium hydroxide, potassium hydroxide and calcium hydroxide, or of an alkali metal salt or alkaline earth metal salt of a compound of the formula III or IIIa or of an organic tertiary nitrogen base, such as of a trialkylamine, for example of triethylamine or trimethylamine, or of an aromatic nitrogen base, for example of pyridine or quinoline, especially of an alkali metal hydride or alkali metal amide. The isomerisation is advantageously carried out in an inert solvent, preferably in an inert polar solvent, for example in acetonitrile, dimethylsulphoxide, tetramethylurea, a higher-boiling ether, such as dioxane, diphenyl ether of diisopropyl ether, an ether of ethylene glycol or tetrahydrofurane, in water, a higher alcohol, an organic tertiary nitrogen base, such as a trialkylamine, for example in triethylamine or trimethylamine, or an aromatic nitrogen base, for example in pyridine or quinoline.

In resulting compounds, substituents can be introduced, modified or split off, within the framework of the definition of the final substances.

Thus, compounds of the formula I which contain a nitro group as the radical $R_2$, can be rearranged in a surprising manner into the corresponding 4-nitroimidazoles, that is to say those compounds of the formula I which contain a nitro group as the radical $R_1$. This rearrangement takes place in a novel manner by the action of an alkali iodide, especially of potassium iodide, preferably in a molar excess, and in the presence of an inert solvent, above all a solvent having polar functional groups, such as dimethylformamide, dimethylacetamide, dimethylsulphoxide, acetonitrile or hexamethylphosphoric acid triamide.

The rearrangement of $R_2$=nitro into $R_1$=nitro compounds of the formula I can also be effected by the action of an iodide which corresponds to the radical $R_3$, $R_3I$, such as, for example, the action of methyl iodide on compounds of the formula I which contain a methyl group as the $R_3$ radical. In this rearrangement, the unsubstituted nitrogen atom of the imidazole ring is quaternised. Thereafter the quaternised salt is pyrolysed. This rearrangement also takes place, for example, in the presence of an inert solvent, preferably those described above.

Depending on the process conditions and the starting substances, the final substances are obtained in the free form or in the form of their acid addition salts which is also included in the invention. Thus, for example, basic, neutral or mixed salts, and if appropriate also hemihydrates, monohydrates, sesquihydrates or polyhydrates thereof, can be obtained. The acid addition salts of the new compounds can be converted into the free compound in a manner which is in itself known, for example with basic agents, such as alkalis or ion exchangers. On the other hand, the resulting free bases can form salts with organic or inorganic acids. In particular, those acids are used for the manufacture of acid addition salts which are suitable for forming therapeutically usable salts. As examples of such acids there may be mentioned: hydrogen halide acids, sulphuric acids, phosphoric acids, nitric acid, perchloric acid, aliphatic, alicyclic, aromatic or heterocyclic carboxylic acids or sulphonic acids, such as formic acid, acetic acid, propionic acid, succinic acid, glycollic acid, lactic acid, malic acid, tartaric acid, citric acid, asoorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicylic acid, embonic acid, methanesulphonic acid, ethanesulphonic acid, hydroxyethanesulphonic acid and ethylenesulphonic acid; halogenobenzenesulphonic acid, toluenesulphonic acid, naphthalenesulphonic acid or sulphanilic acid; methionine, tryptophane, lysine or arginine.

These or other salts of the new compounds such as, for example, the picrates can also serve for the purification of the resulting free bases by converting the free bases into salts, isolating these and again liberating the bases from the salts. Because of the close relationships between the new compounds in the free form and in the form of their salts the free compounds are to be understood, in the preceding and following text, where appropriate also to include the corresponding salts in general sense and intended use.

The invention also relates to those embodiments of a process in which a process is stopped at any stage or in which a compound obtainable as an intermediate product at any stage is used as the starting product and the missing steps are carried out, or in which a starting substance is used in the form of a salt and/or racemate or antipode or, in particular, is formed under the reaction conditions.

Depending on the number of the asymmetrical C atoms and the choice of the starting substances and procedures, the new compounds can be in the form of racemate mixtures, racemates or optical antipodes.

Racemate mixtures can be separated into the pure racemates on the basis of the physico-chemical differences of the constituents in a known manner, for example by chromatography and/or fractional crystallisation.

The separation of racemates obtained into the optical antipodes can be carried out in a manner which is in itself known. Resulting racemates can, for example, be converted into esters of optically active acids, or preferably, into salts with optically active acids. Particularly customary optically active acids are, for example, the D- and L- forms of tartaric acid, di-o-toluyltartaric acid, diacetyl-tartaric acid, malic acid, mandelic acid, camphoric acid, camphorsulphonic acid, bromocamphorsulphonic acid and quinic acid.

The resulting mixtures of diastereoisomeric salts are separated into the individual salts on the basis of physicochemical differences, for example in solubility, crystallisability and the like, and the optically active antipodes are liberated from the salts. Furthermore, a resulting racemate in the salt form can be reacted with an optically active metal complex salt or a resulting racemate in the free form can be reacted with an optically active metal complex hydroxide, and the less soluble product can be separated off and the optically pure compound liberated. Suitable optically active metal complexes are, for example, optically active cobalt nitrate complex compounds.

It is furthermore also possible to separate racemates obtained into the optically active antipodes by fractional crystallisation, if appropriate from an optically active solvent, or by chromatography, especially thin layer chromatography, on an optically active carrier, or with the aid of microorganisms. Mixtures of diastereoisomeric compounds are separated into the pure isomeric compounds in the customary manner on the basis of their physico-chemical differences, such as those of solubility, boiling points and the like, for example by fractional crystallisation or distillation. Herein, the pharmacologically more active pure isomer, especially the more active or less toxic antipode, is advantageously isolated.

According to the invention it is, however, also possible to obtain the end products in the form of the pure racemates or optical antipodes by employing the starting substances containing one or more asymmetrical C atoms in the form of the pure racemates or optical antipodes.

The starting substances are known or can, if they are new, be obtained according to methods which are in themselves known. Appropriately, those starting substances are used for carrying out the reactions according to the invention as lead to the initially particularly mentioned groups of final substances and particularly to the final substances which have been especially described and singled out.

Thus, the 4- or 5-nitroimidazoles of the formula IV which have been mentioned as starting substances can be obtained, for example, by condensing a compound of formula II

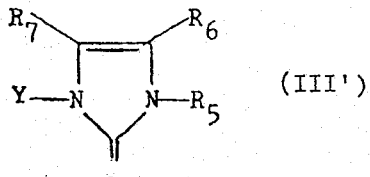

with a compound of the formula III' or IIIa'

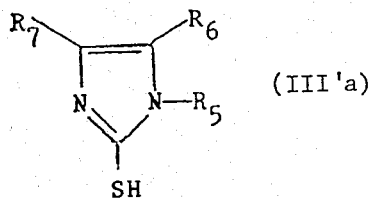

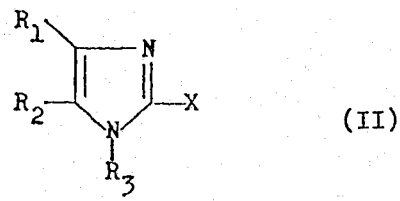

wherein $R_1$, $R_2$, $R_3$, $R_4$, $R_5$, $R_6$, $R_7$ and X have the indicated meanings.

The reaction can be carried out in the usual manner. Thus, for example, when starting from starting substances wherein X is one of the radicals X which have been mentioned, the reaction is preferably carried out in the presence of a basic condensation agent, or the compound of the formula IIIa or III' is reacted in the form of a N-metal derivative, such as, for example, an alkali metal derivative, which is obtainable, for example, from a compound of the formula III or IIIa and a strong base, for example an amide, a hydrocarbon compound, an alcoholate, the hydroxide or especially the hydride of an alkali metal, such as of lithium, potassium or above all sodium, or from this metal itself, and can be used without isolation. Examples of basic condensation agents are alkali metal hydroxides or alkaline earth metal hydroxides, such as sodium, potassium and calcium hydroxide or organic tertiary nitrogen bases, such as trialkylamines, for example triethylamine or trimethylamine, or aromatic nitrogen bases, for example, pyridine or quinoline. Advantageously, the reaction is carried out at elevated temperature and/or in the presence of an inert solvent, especially an inert solvent with polar groups, for example acetonitrile, dimethylsulphoxide, dimethylformamide, tetramethylurea, a higher-boiling ether, such as diphenyl ether, diisopropyl ether and ethers of ethylene glycol, water, a higher alcohol, one of the nitrogen bases mentioned or especially tetrahydrofurane or dioxane.

Depending on the starting substances used and the process conditions, the 4- or 5-nitroimidazoles according to the invention, of the formula I

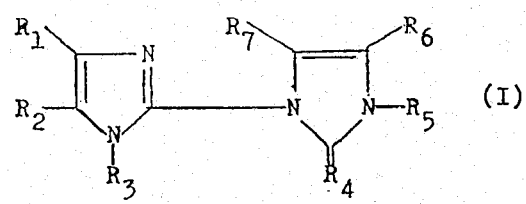

are also obtained alongside the 4- or 5-nitroimidazoles of the formula IV which have been mentioned as starting substances.

The yield of these final substances according to the invention can be increased or reduced by suitable choice of the reaction conditions. Additionally it is generally not necessary to remove these substances before carrying out the isomerisation reaction which has been described.

The new compounds can be used, for example, in the form of pharmaceutical preparations in which they are present in the free form or optionally in the form of their salts, especially of the therapeutically usable salts, mixed with a pharmaceutical, organic or inorganic, solid or liquid excipient which is suitable, for example, for enteral or parenteral administration. Suitable substances for forming the excipient are those which do not react with the new compounds such as, for example, water, gelatine, lactose, starch, stearyl alcohol, magnesium stearate, talc, vegetable oils, benzyl alcohols, gum, propylene glycols, white petroleum jelly or other known medicinal excipients. The pharmaceutical preparations can, for example, be in the form of tablets, dragees, capsules or suppositories or in a liquid form, as solutions (for example as an elixir or syrup), suspensions or emulsions. If appropriate, they are sterilised and/or contain auxiliaries, such as preservatives, stabilisers, wetting agents or emulsifiers, solubilising agents or salts for regulating the osmotic pressure or buffers. They can also contain other therapeutically valuable substances. The pharmaceutical preparations are obtained according to customary methods. The dosage of the new compounds can vary depending on the compound and on the individual requirements of the patient. The customary daily dose for a warm-blooded animal weighing approx. 75 kg is between about 0.25 and 1.0 g.

The new compounds can also be used in veterinary medicine, for example in one of the abovementioned forms or in the form of feedstuffs or of additives to animal fodder. Here, for example, the customary extenders and diluents or feedstuffs are used.

The invention is described in more detail in the examples which follow.

EXAMPLE 1

A solution of 11.4 g of 2-mercapto-1-methyl-imidazole in 60 ml of dimethylformamide is added dropwise over the course of 15 minutes to a suspension of 4.8 g of 50% strength sodium hydride in 100 ml of dimethylformamide at 20° to 30°C, whilst stirring. The resulting solution is then added dropwise over the course of 30 minutes to a solution of 20.5 g of 1-methyl-2-methylsulphonyl-5-nitro-imidazole in 80 ml of dimethylformamide at 20° to 30°C whilst stirring. The resulting solution is then added dropwise over the course of 30 minutes to a solution of 20.5 g of 1-methyl-2-methylsulphonyl-5-nitro-imidazole in 80 ml of dimethylformamide at 20 to 30° C) whilst stirring. Thereafter the reaction mixture is stirred for a further hour at 100°C and is evaporated. The evaporation residue is extracted by shaking with 200 ml of methylene chloride and 200 ml of water and the methylene chloride extract is separated off, washed with 50 ml of water, dried over anhydrous magnesium sulphate and evaporated. After two recrystallisations from ethyl acetate the evaporation residue yields pure 1-methyl-2-[(1-methyl-5-nitro-2-imidazolyl)mercapto]-imidazole of melting point 123°–124°C.

The combined mother liquors of the crystallisation are evaporated and separated on a chromatography column of 50 mm diameter, filled with 550 g of silica gel. Elution is carried out with methylene chloride and fractions of 600 ml each are collected. The 17th to 24th fraction are combined and evaporated and the residue is recrystallised from 85 ml of absolute ethanol. Pure 1-methyl-3-(1-methyl-5-nitro-2-imidazolyl)-4-imidazoline-2-thione of the formula

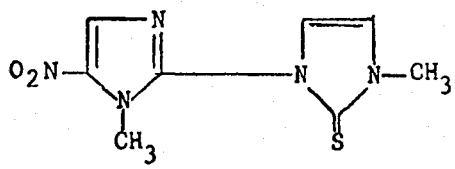

and of melting point 180°–181°C is thus obtained.

The 1-methyl-2-[(1-methyl-5-nitro-2-imidazolyl)-mercapto]-imidazole constituents still present on the column can be eluted with chloroform and be combined with the main quantity, after evaporation.

EXAMPLE 2

A solution of 12.0 g of 1-methyl-2-[(1-methyl-5-nitro-2-imidazolyl)-mercapto]-imidazole in 80 ml of dimethylformamide is treated with 0.3 g of 50% strength sodium hydride and heated to 90°–100°C for 5 hours whilst stirring. Thereafter the reaction mixture is evaporated and the evaporation residue is taken up in 150 ml of ethylene chloride. The resulting solution is washed five times with 50 ml of water at a time, dried over anhydrous magnesium sulphate and evaporated, and chromatographed on a column of 40 mm diameter filled with 300 g of silica gel. Elution is carried out with methylene chloride and fractions of 600 ml are collected. The 9th to 12th fraction are combined and recrystallised from 200 ml of ethanol. Pure 1-methyl-3-(1-methyl-5-nitro-2-imidazolyl)-4-imidazoline-2-thione of melting point 180°–181°C, which is identical with the product obtained in Example 1, is thus obtained.

EXAMPLE 3

A solution of 7.5 g of 1-phenyl-2-[(1-methyl-5-nitro-2-imidazolyl)-mercapto]-imidazole in 75 ml of dimethylformamide is treated with 0.2 g of 50% strength sodium hydride and heated to 90°–100°C for 20 hours whilst stirring. Thereafter the reaction mixture is evaporated and the evaporation residue is taken up in 150 ml of ethylene chloride and extracted by shaking five times with 50 ml of water at a time. The ethylene chloride extract is dried with anhydrous magnesium sulphate and evaporated, and the evaporation residue is chromatographed on a column of 40 mm diameter filled with 300 g of silica gel. Elution is carried out with methylene chloride and fractions of approx. 500 ml are collected. Fractions No. 12–15 are combined and recrystallised from 400 ml of alcohol. 1-Phenyl-3-(1-methyl-5-nitro-2-imidazolyl)-4-imidazoline-2-thione of the formula

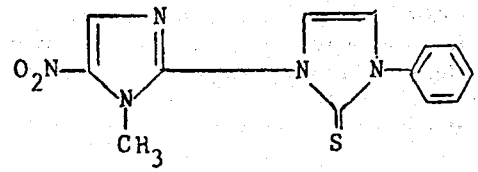

and of melting point 204°–205°C is thus obtained.

The 1-phenyl-2-[(1-methyl-5-nitro-2-imidazolyl)-mercapto]-imidazole used as the starting material can be manufactured, for example, by condensation of 1-methyl-2-methylsulphonyl-5-nitroimidazole with 1-phenyl-2-mercapto-imidazole in dioxane, using sodium hydride. It melts at 160°–161°C (from 2-ethoxyethanol).

EXAMPLE 4

11.5 g of 1-methyl-3-(1-methyl-5-nitro-2-imidazolyl)-4-imidazoline-2-thione, 30 g of potassium iodide and 160 ml of dimethylformamide are heated under reflux for 15 hours. After cooling, the reaction mixture is treated with 1,000 ml of water and the product which has precipitated is filtered off and washed first with water and then with isopropanol. The crude product thus obtained, which melts at 236°–238°C, is recrystallised from 225 ml of 2-ethoxyethanol. 1-Methyl-3-(1-methyl-4-nitro-2-imidazolyl)-4-imidazoline-2-thione of the formula

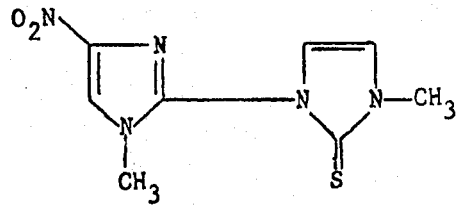

and of melting point 241°–234°C is thus obtained.

EXAMPLE 5

Tablets containing 250 mg of active substance are manufactured in the customary manner, for example to have the following composition per tablet:

Composition

| | |
|---|---|
| 1-Methyl-3-(1-methyl-5-nitro-2-imidazolyl)-4-imidazoline-2-thione | 250 mg |
| Lactose | 36 mg |
| Wheat starch | 100 mg |
| Colloidal silica | 16 mg |
| Talc | 16 mg |
| Magnesium stearate | 2 mg |
| | 420 mg |

Manufacture

1-Methyl-3-(1-methyl-5-nitro-2-imidazolyl)-4-imidazoline-2-thione is mixed with the lactose, a part of the wheat starch and colloidal silica and the mixture is rubbed through a sieve, whereby a powder mixture is obtained. A further part of the wheat starch is worked into a paste with a five-fold amount of water on a water-bath and the powder mixture is kneaded with this paste until a slightly plastic mass has been produced.

The plastic mass is forced through a sieve of approx. 3 mm mesh width and dried, and the dry granules are again forced through a sieve. Thereafter the remaining wheat starch, talc and magnesium stearate are mixed in and the resulting mixture is pressed to give tablets weighing 420 mg (and having a breaking notch).

What we claim is:

1. An imidazole compound of the formula

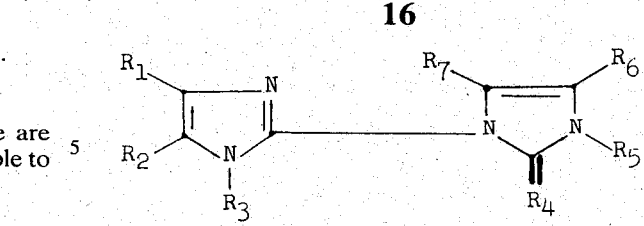

wherein one of $R_1$ and $R_2$ is hydrogen or lower alkyl and the other is nitro, $R_3$ is hydrogen, lower alkyl, hydroxy-lower alkyl, lower alkoxy-lower alkyl $R_4$ is oxo or thioxo, $R_5$ is hydrogen, lower alkyl, hydroxy-lower alkyl, lower alkoxy-lower alkyl, phenyl or monosubstituted phenyl substituted by lower alkyl, lower alkoxy, halogen or trifluoromethyl, and $R_6$ and $R_7$ conjointly form the missing part of a fused benzene nucleus or a benzene nucleus substituted by lower alkyl, lower alkoxy, halogen, trifluoromethyl or a nitro group, and the S-oxides, sulfones, N-oxides or acid addition salts thereof.

2. The compound of claim 1, wherein $R_1$ represents hydrogen, $R_2$ represents a nitro group, $R_3$ represents lower alkyl, $R_4$ represents oxo or thioxo, $R_5$ represents hydrogen or lower alkyl and $R_6$ and $R_7$ have the same meaning as in claim 13.

3. 1-Methyl-3-(1-methyl-5-nitro-2-imidazolyl)-benzimidazol-2-(3H)-one or an acid addition salt thereof.

4. 1-Methyl-3-(1-methyl-5-nitro-2-imidazolyl)-benzimidazole-2-(3H)-thione or an acid addition salt thereof.

* * * * *